(12) United States Patent
Dugi et al.

(10) Patent No.: US 8,202,884 B2
(45) Date of Patent: Jun. 19, 2012

(54) TREATMENT OF TYPE 2 DIABETES

(75) Inventors: Klaus Dugi, Dresden (DE); Andreas Raschig, Biberach (DE); Juergen Reess, Ulm (DE); Frank Berger, Frankfurt (DE); Laurence Salin, Reims (FR)

(73) Assignee: Neurosearch A/S, Ballerup (DK)

( * ) Notice: Subject to any disclaimer, the term of this patent is extended or adjusted under 35 U.S.C. 154(b) by 704 days.

(21) Appl. No.: 12/091,885

(22) PCT Filed: Oct. 31, 2006

(86) PCT No.: PCT/EP2006/010476
§ 371 (c)(1),
(2), (4) Date: Aug. 28, 2008

(87) PCT Pub. No.: WO2007/051594
PCT Pub. Date: May 10, 2007

(65) Prior Publication Data
US 2009/0018159 A1 Jan. 15, 2009

(30) Foreign Application Priority Data

Oct. 31, 2005 (EP) .................................. 05023794

(51) Int. Cl.
*A61K 31/44* (2006.01)
*A61K 31/55* (2006.01)
*A61K 31/535* (2006.01)
*A61K 31/445* (2006.01)

(52) U.S. Cl. ................. 514/304; 514/217.09; 514/236.5; 514/326; 514/866

(58) Field of Classification Search .................. 514/304, 514/326, 217.09, 236.5, 866
See application file for complete search history.

(56) References Cited

U.S. PATENT DOCUMENTS

| 5,444,070 | A | 8/1995 | Moldt et al. | |
| 6,288,079 | B1 * | 9/2001 | Scheel-Kruger et al. | 514/304 |
| 7,230,001 | B1 | 6/2007 | Rudolf et al. | |
| 7,459,464 | B2 * | 12/2008 | Scheel-Kruger et al. | 514/304 |
| 2003/0153752 | A1 | 8/2003 | Hirst et al. | |
| 2004/0054173 | A1 | 3/2004 | Kimura et al. | |

FOREIGN PATENT DOCUMENTS

| EP | 0 604 352 A2 | 6/1994 |
| EP | 0 604 354 A2 | 6/1994 |
| EP | 0 604 355 A2 | 6/1994 |
| WO | WO-93/09814 A1 | 5/1993 |
| WO | WO-95/28401 A1 | 10/1995 |
| WO | WO-97/30997 A1 | 8/1997 |
| WO | WO-01/32649 A1 | 5/2001 |
| WO | WO-03/076398 A2 | 9/2003 |
| WO | WO-03/101453 A1 | 12/2003 |
| WO | WO-2004/072071 A1 | 8/2004 |
| WO | WO-2004/072075 A1 | 8/2004 |
| WO | WO-2004/113334 A1 | 12/2004 |
| WO | WO-2005/011694 A1 | 2/2005 |
| WO | WO-2005/070427 A1 | 8/2005 |

OTHER PUBLICATIONS

Siddall, R., RIO-Diabetes: rimonabant shows promise in type 2 diabetes, *British Journal of Cardiology*, Jul. 2005, vol. 12, No. 4, p. 257.

* cited by examiner

*Primary Examiner* — Kevin E Weddington
(74) *Attorney, Agent, or Firm* — Birch, Stewart, Kolasch & Birch, LLP

(57) ABSTRACT

The invention relates to the use of a monoamine neurotransmitter re-uptake inhibitor comprising a 2,3-disubstituted tropane moiety, or a tautomer, a pharmaceutically acceptable salt, solvate, or physiologically functional derivative thereof for the manufacture of a medicament for the treatment of diabetic patients.

13 Claims, No Drawings

TREATMENT OF TYPE 2 DIABETES

BACKGROUND OF THE INVENTION

1. Technical Field

The invention relates to the use of a monoamine neurotransmitter re-uptake inhibitor comprising a 2,3-disubstituted tropane moiety, or a tautomer, a pharmaceutically acceptable salt, solvate, or physiologically functional derivative thereof for the manufacture of a medicament for the treatment of diabetes.

2. Background Information

The incidence of diabetes and in turn the incidence of diseases arising from diabetes is constantly increasing. The reasons for this increase are subject to discussion but it is believed that Western life style as well as of a shift in the ageing statistics contributes. Diabetes, type-2 diabetes, diabetes mellitus respectively, is a metabolic disease with an increase of the level of blood glucose above the range of normal subjects. The disease evolves if there is quantitative insufficiency or functional insufficiency of insulin in bodies. Among the severe consequences of the disease microangiopathy in kidney, retina, nerve and great vessel disorders such as arteriosclerosis are to be named which more or less creepingly destroy the functionality of the tissues and organs involved. Hyperglycemic states, which characterize the disease, arise most often after meals, between meals or even during fasting.

To counteract or at least to delay such diabetic destruction there have been developed several drugs basing on different mode of actions. Antidiabetics, most often hypoglycemic agents, include insulin, insulin secretion-promoting agents, insulin resistance-ameliorating agents and alpha-glucosidase inhibitors. The objective of the most prominent of them is more or less to create a constant blood-level of glucose. Although useful, these compounds may loose effect when the disease develops further. Additionally, the treatments are not free from side effects. Accordingly, there is a need to complement or to supplement the treatment options in diabetes or even better to find drugs or drug combinations with a superior efficacy-safety-profile.

The International patent applications WO 93/09814 and WO 97/30997 disclose tropane derivatives, which are monoamine neurotransmitter re-uptake inhibitors. Such compounds are disclosed to be useful for the treatment of parkinsonism, depression, narcolepsy, drug abuse, attention-deficit hyperactivity disorders, senile dementia and cognitive dysfunction. WO 05/070427 teaches that the mentioned monoamine neurotransmitter re-uptake inhibitors may be used to reduce body weight with a sustaining effect in healthy persons as well as in persons suffering from metabolic diseases.

BRIEF SUMMARY OF THE INVENTION

According to the present invention monoamine neurotransmitter re-uptake inhibitors, in particular such inhibitors which comprise a 2,3-disubstituted tropane moiety, are useful in the treatment of diabetes. Additionally, the compounds may be used in associated diseases which develop as a consequence of diabetes and that are sensitive to the monoamine neurotransmitter reuptake-inhibiting activity.

Accordingly, it is an objective of the invention to develop a new therapeutic treatment option for diabetes.

Another objective is to develop a complementary treatment option to the prior art treatment options.

Again another objective is to develop a supplemental (add-on) treatment option to the prior art treatment options.

DETAILED DESCRIPTION OF THE INVENTION

As a rule, preferred monoamine neurotransmitter re-uptake inhibitor which are of interest in the context of this invention comprise a 2,3-disubstituted tropane moiety and are disclosed by international patent applications WO 93/09814, EP 604355, EP 604352, U.S. Pat. No. 5444070, EP 604354, WO 95/28401 and WO 97/30997. Of particular interest are WO 93/09814 and WO 97/30997.

For the sake of clarity, it will be evident for the skilled reader that the present compounds disclosed might have tautomeric forms or will be applied in form of a pharmaceutically acceptable salt, solvate, or a physiologically functional derivative thereof. Any such forms shall be comprised even if they are not mentioned by name.

For the intended use according to the invention, the compounds of the general formula (I) or a pharmaceutical acceptable addition salt thereof or the N-oxide thereof are preferred.

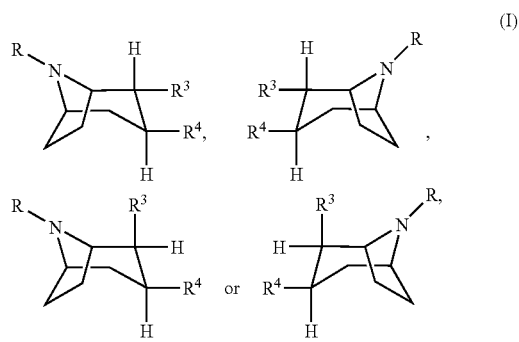

(I)

whereby (A)
(i) R is hydrogen, alkyl, alkenyl, alkynyl, cycloalkyl, cycloalkylalkyl or 2-hydroxyethyl; or
(ii) R represents a hydrogen atom or a $C_{1-6}$ alkyl group, preferably a hydrogen atom, a methyl or an ethyl group; or
(iii) R is hydrogen, methyl, ethyl or propyl; or
(iv) R is H or
(v) R is methyl.

(B)
(i) $R^3$ is —$CH_2$—X—R', wherein X is O, S, or NR"; wherein
   R' is alkyl, alkenyl, alkynyl, cycloalkyl, cycloalkylalkyl, or
     —CO-alkyl; preferably
   X is O and
   R" is hydrogen or alkyl;
   heteroaryl which may be substituted one or more times with
     alkyl, cycloalkyl, or cycloalkylalkyl;
     phenyl which may be substituted one or more times with substituents selected from the group consisting of halogen, $CF_3$, CN, alkoxy, alkyl, alkenyl,
     alkynyl, amino, nitro, and heteroaryl;
     phenylphenyl;
     pyridyl which may be substituted one or more times with substituents selected from the group consisting of halogen, $CF_3$, CN, alkoxy, alkyl, alkenyl, alkynyl, amino, nitro, and heteroaryl;
     thienyl which may be substituted one or more times with substituents selected from the group consisting of halogen, $CF_3$, CN, alkoxy, alkyl, alkenyl, alkynyl, amino, nitro, and heteroaryl; or benzyl which may be substituted one or more times with substituents selected from the group consisting of halogen, $CF_3$, CN, alkoxy, alkyl, alkenyl, alkynyl, amino, nitro, and heteroaryl; or —$(CH_2)_nCO_2R^{11}$, $COR^{11}$, or $CH_2R^{12}$, wherein $R^{11}$ is alkyl, cycloalkyl, or cycloalkylalkyl; phenyl which may be substituted one or more times with substituents selected from the group consisting of halogen, $CF_3$, CN, alkoxy, alkyl, alkenyl, alkynyl, amino, nitro, and heteroaryl; phenylphenyl; pyridyl which may be substituted one or more times with substituents selected from the group consisting of halogen, $CF_3$, CN, alkoxy, alkyl, alkenyl, alkynyl, amino, nitro, and heteroaryl; or thienyl which may be substituted one or more times with substituents selected from the group consisting of halogen, $CF_3$, CN, alkoxy, alkyl, alkenyl, alkynyl, amino, nitro, and heteroaryl; or benzyl;

n is 0 or 1; and $R^{12}$ is O-phenyl which may be substituted one or more times with substituents selected from the group consisting of halogen, $CF_3$, CN, alkoxy, alkyl, alkenyl, alkynyl, amino, nitro, and heteroaryl; or O—CO-phenyl which may be substituted one or more times with substituents selected from the group consisting of halogen, $CF_3$, CN, alkoxy, alkyl, alkenyl, alkynyl, amino, nitro, and heteroaryl; or CH=NOR'; wherein R' is o hydrogen; o alkyl, cycloalkyl, cycloalkylalkyl, alkenyl, alkynyl or aryl; all of which may be substituted with —COOH; —COO-alkyl; —COO-cycloalkyl; or phenyl which may be substituted one or more times with substituents selected from the group consisting of halogen, $CF_3$, CN, alkyl, cycloalkyl, alkoxy, cycloalkoxy, alkenyl, alkynyl, amino, and nitro; or (ii) $R^3$ is —$CH_2$—X—R', wherein X is O, S, or NR"; wherein R" is hydrogen or alkyl; and R' is alkyl, alkenyl, alkynyl, cycloalkyl, cycloalkylalkyl, or —CO-alkyl; or (iii) $R^3$ is —$CH_2$—X—R', wherein X is O or S, and W is methyl, ethyl, propyl, or cyclopropylmethyl; or (iv) $R^3$ is —$CH_2$—X—R', wherein X is O and R' represents a hydrogen atom or a $C_{1-6}$ alkyl or $C_{3-6}$-cycloalkyl-$C_{1-3}$-alkyl group, preferably a methyl, ethyl or n-propyl group; or (v) $R^3$ is —$CH_2$—X—R', with X being O and R' being methyl; or (vi) $R^3$ is —$CH_2$—X—R', with X being O and R' being ethyl; or (vii) $R^3$ is —CH=NOR'; wherein R' is hydrogen; alkyl, cycloalkyl, cycloalkylalkyl, alkenyl, alkynyl or aryl; all of which may be substituted with —COOH; —COO-alkyl; —COO-cycloalkyl; or phenyl which may be substituted one or more times with substituents selected from the group consisting of halogen, $CF_3$, CN, alkyl, cycloalkyl, alkoxy, cycloalkoxy, alkenyl, alkynyl, amino, and nitro; or (viii) $R^3$ is —CH=NOR'; wherein R' is hydrogen or alkyl, or 1,2,4-oxadiazol-5-yl which may by substituted in the 3 position with alkyl.

(C)

(i) $R^4$ is phenyl, 3,4-methylenedioxyphenyl, benzyl, naphthyl, or heteroaryl all of which may be substituted one or more times with substituents selected from the group consisting of halogen, $CF_3$, CN, alkoxy, cycloalkoxy, alkyl, cycloalkyl, alkenyl, alkynyl, amino, nitro, and heteroaryl; or (ii) $R^4$ is phenyl, which is substituted once or twice with substituents selected from the group consisting of halogen, $CF_3$, CN, alkoxy, cycloalkoxy, allyl, cycloalkyl, alkenyl, alkynyl, amino, nitro, and heteroaryl; or (iii) $R^4$ is phenyl substituted m times by a halogen atom or a $CF_3$ or cyano group, preferably a fluorine, chlorine or bromine atom; and m is 0 or an integer from 1 to 3, preferably 1 or 2; or (iv) $R^4$ is phenyl substituted once or twice with chlorine; or (v) is 3,4-dichlorophenyl.

In a preferred embodiment of the invention, the tropane derivative having dopamine reuptake inhibitor activity is a (1R,2R,3S)-2,3-disubstituted tropane derivative of formula I.

Preferred embodiments include, but are not limited to the following substituent patterns:

| Embodiment | R | $R^3$ | $R^4$ |
|---|---|---|---|
| I-1 | Ai | Bi | Ci |
| I-2 | Ai | Bii | Ci |
| I-3 | Ai | Biii | Ci |
| I-4 | Ai | Biv | Ci |
| I-5 | Ai | Bv | Ci |
| I-6 | Ai | Bi | Cii |
| I-7 | Aii | Bi | Ci |
| I-8 | Aii | Bii | Ci |
| I-9 | Aii | Biii | Ci |
| I-10 | Aii | Biv | Ci |
| I-11 | Aii | Bv | Ci |
| I-12 | Aii | Bi | Cii |
| I-13 | Aiv | Bv | Cv |
| I-14 | Aiv | Bvi | Cv |
| I-15 | Av | Bv | Cv |
| I-16 | Av | Bvi | Cv |
| I-17 | Ai | Bvi | Ci |

Preferably those monoamine neurotransmitter re-uptake inhibitor comprising a 2,3-disubstituted tropane moiety are compounds of formula (I1)

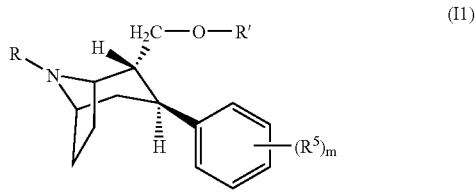

(I1)

wherein $R^5$ each independently represents a halogen atom or a $CF_3$ or cyano group, preferably a fluorine, chlorine or bromine atom;

R' represents a hydrogen atom or a $C_{1-6}$ alkyl or $C_{3-6}$-cycloalkyl-$C_{1-3}$-alkyl group, preferably a methyl, ethyl or n-propyl group; and m is 0 or an integer from 1 to 3, preferably 1 or 2;

or a tautomer, a pharmaceutically acceptable salt, solvate, or physiologically functional derivative thereof.

As used herein, the expression "alkyl" preferably means "$C_{1-6}$ alkyl" which includes methyl and ethyl groups, and straight-chained and branched propyl, butyl, pentyl and hexyl groups. Particularly preferred alkyl groups are methyl, ethyl, n-propyl, isopropyl and tert.-butyl.

The expression "cycloalkyl" as used herein preferably means "$C_{3-6}$ cycloalkyl" which includes cyclic propyl, butyl, pentyl and hexyl groups such as cyclopropyl and cyclohexyl.

The term "halogen" as used herein includes fluorine, chlorine, bromine and iodine, of which fluorine and chlorine are preferred.

Further abbreviations:
H stands for hydrogen, Me for methyl, Et for ethyl, Pr for propyl, Bu for butyl, Ph for phenyle, Bn for benzyle (which is PhCH$_2$—), F for fluoro, Cl for chloro, Br for bromo, Ox for 1,2,4-oxadiazol-5-yl, Cy for cyclopropyl, Fu for furanyl, Py for pyridyl, Th for thienyl.
For example, 4-F-Ph stands for a 4-fluorophenyle-group, the abbreviation 3,4-C$_{12}$-Ph stands for a 3,4-dichlorophenyle-group.
If other abbreviations are used, they will be well known in the art.

The term "physiologically functional derivative" as used herein includes derivatives obtained from the compound of formula (I) under physiological conditions, these are for example N-oxides, which are formed under oxidative conditions.

The term "pharmaceutically acceptable acid addition salt" as used herein includes those salts which are selected from among the acid addition salts formed with hydrochloric acid, hydrobromic acid, sulphuric acid, phosphoric acid, methane-sulphonic acid, acetic acid, fumaric acid, succinic acid, lactic acid, citric acid, tartaric acid and maleic acid, the salts obtained from hydrochloric acid, hydrobromic acid, sulphuric acid, phosphoric acid and acetic acid being particularly preferred. The salts of citric acid are of particular significance.

In a special embodiment, the tropane derivative having dopamine reuptake inhibitor activity is a compound of the general formula (II) selected from:

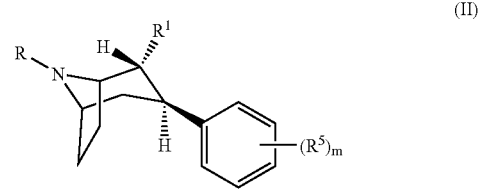

(II)

with

| R | R$^1$ | (R$^5$)$_m$ together with the phenylgroup it is attached to stands for | No |
|---|---|---|---|
| Me | 3-Cy-Ox- | 4-F-Ph | 1 |
| Me | 3-Ph-Ox- | 4-F-Ph | 2 |
| Me | 3-Ph-Ox- | 4-Me-Ph | 3 |
| Me | 3-Bn-Ox- | 4-F-Ph | 4 |
| Me | 3-(4-Ph-Ph)-Ox- | 4-F-Ph | 5 |
| Me | 4-F-Ph-CO— | 4-F-Ph | 6 |
| Me | —CH=N—OH | 3,4-Cl$_2$-Ph | 7 |
| Me | —CH=N—OCH$_3$ | 3,4-Cl$_2$-Ph | 8 |
| Me | —CH=N—OBn | 3,4-Cl$_2$-Ph | 9 |
| Me | —CH=N—OCH$_2$—CO—OEt | 3,4-Cl$_2$-Ph | 10 |
| Me | —CH=N—OCH$_2$—CO—OMe | 3,4-Cl$_2$-Ph | 11 |
| Me | —CH=N—OC(CH$_3$)$_2$—CO—OEt | 3,4-Cl$_2$-Ph | 12 |
| Me | —CH=N—OCH$_2$—CO—OH | 3,4-Cl$_2$-Ph | 13 |
| H | —CH=N—OCH$_3$ | 3,4-Cl$_2$-Ph | 14 |
| H | —CH=N—OBn | 3,4-Cl$_2$-Ph | 15 |
| Me | —CH=N—OCH$_3$ | 4-Me-Ph | 16 |
| Me | —CH=N—OC(CH$_3$)$_3$ | 3,4-Cl$_2$-Ph | 17 |
| Me | —CH=N—OCH$_3$ | 4-Cl-Ph | 18* |
| Me | —CH=N—OCH$_2$—CO—OMe | 4-Cl-Ph | 19 |
| Me | —O-(2-propynyl)-aldoxime | 3,4-Cl$_2$-Ph | 20 |
| Me | —CH=N—OCH$_2$—C(—CH$_3$)H—CH$_3$ | 3,4-Cl$_2$-Ph | 21 |
| Me | —CH=N—OCH$_2$Cy | 3,4-Cl$_2$-Ph | 22 |
| Me | —CH=N—OEt | 3,4-Cl$_2$-Ph | 23 |
| Me | —CH$_2$—O—CH(CH$_3$)$_2$ | 3,4-Cl$_2$-Ph | 24 |
| Me | —CH$_2$—O—CH$_3$ | 3,4-Cl$_2$-Ph | 25 |
| Me | —CH$_2$-O-Et | 3,4-Cl$_2$-Ph | 26 |
| Me | —CH$_2$—O—CH$_2$—Cy | 3,4-Cl$_2$-Ph | 27 |
| Me | —CH$_2$—O—CH$_3$ | 4-Cl-Ph | 28 |
| H | —CH$_2$—O—CH$_3$ | 4-Cl-Ph | 29 |
| Me | —CH$_2$-O-Et | 4-Cl-Ph | 30 |
| H | —CH$_2$—O—CH$_3$ | 3,4-Cl$_2$-Ph | 31 |
| H | —CH$_2$-O-Et | 3,4-Cl$_2$-Ph | 32 |
| H | —CH$_2$-O-Et | 4-Cl-Ph | 33 |
| H | —CH$_2$—O—CH$_2$—Cy | 4-Cl-Ph | 34 |
| Me | —CH$_2$—O—CH$_2$—Cy | 4-Cl-Ph | 35 |
| Me | —CH$_2$—S-Et | 3,4-Cl$_2$-Ph | 36 |
| Me | —CH$_2$—OH | 4-F-Ph | 37 |
| Me | —CH$_2$—OH | 3,4-Cl$_2$-Ph | 38 |
| —CO—O—C(CH$_3$)$_3$ | —CH$_2$—OH | 3,4-Cl$_2$-Ph | 39 |
| Me | —CH$_2$—OH | 4-Cl-Ph | 40 |
| Me | 3-(2-Fu)-Ox- | 3,4-Cl$_2$-Ph | 41 |
| Me | 3-(3-Py)—Ox- | 3,4-Cl$_2$-Ph | 42 |
| —CH$_2$—CH$_2$=CH$_2$ | 3-(4-Py)—Ox | 3,4-Cl$_2$-Ph | 43 |
| Et | 3-(4-Py)—Ox- | 3,4-Cl$_2$-Ph | 44 |
| —CH$_2$—CH$_2$OH | 3-(4-Py)—Ox- | 3,4-Cl$_2$-Ph | 45 |
| H | 3-(4-Py)—Ox- | 3,4-Cl$_2$-Ph | 46 |
| —CH$_2$—CH$_2$=CH$_2$ | 3-(3-Py)—Ox- | 3,4-Cl$_2$-Ph | 47 |
| Me | 3-(2-Th)—Ox- | 4-Cl-Ph | 48 |
| Me | 3-(2-Th)—Ox | 3,4-Cl$_2$-Ph | 49 |

-continued

| R | R¹ | $(R^5)_m$ together with the phenylgroup it is attached to stands for | No |
|---|---|---|---|
| Me | 3-(4-Py)-Ox | 3,4-Cl$_2$-Ph | 50 |
| Me | 3-(2-Py)-Ox- | 3,4-Cl$_2$-Ph | 51 |
| Me | 3(4-Py)-Ox- | 4-Cl-Ph | 52 |
| Me | 3-(3-Py)-Ox- | 4-Cl-Ph | 53 |
| Me | 3-(2-Py)-Ox- | 4-Cl-Ph | 54 |
| Me | 3-Ph-Ox- | 4-F-Ph | 55 |
| Me | 3-Ph-Ox- | 4-Me-Ph | 56 |
| Me | 3-Bn-Ox- | 4-F-Ph | 57 |
| Me | 3-(4-Ph-Ph)-Ox- | 4-F-Ph | 58 |
| Me | 3-(3-Ph)-Ox- | | 59 |
| Me | 4-Cl-Ph-O—CH$_2$— | 4-F-Ph | 60 |
| Me | 4-Cl-Ph-O—CH$_2$— | 3,4-Cl$_2$-Ph | 61 |
| Me | 4-Cl-Ph-O—CH$_2$— | 4-Me-Ph | 62 |
| Me | Ph-CO—O—CH$_2$— | 4-F-Ph | 63 |
| Me | —CO—O—CH$_3$ | 3,4-Cl$_2$-Ph | 64 |
| Me | —CO—O—CH$_3$ | 4-Cl-Ph | 65 |
| Me | —CO—O—CH$_3$ | 4-Me-Ph | 66 |
| Me | —CO—O—CH$_3$ | 4-Ph | 67 |
| Me | —CO—O—CH$_3$ | 4-tert.Bu-Ph | 68 |

*as well as the HCl-salt thereof as well as
(1 R, 2R, 3S)-2-(3-Phenyl-1,2,4-oxadiazol-5-yl)-3-(2-naphthyl)-tropane (No. 69);
(1 R, 2R, 3S)-Carbomethxy-3-(2-naphthyl)-tropane (No. 70);
(1 R, 2R, 3S)-2-Carbomethxy-3-benzyl-tropane (No. 71);
(1 R, 2R, 3S)-2-Carbomethxy-3-(1-naphthyl)-tropane (No. 72).

For the sake of clarity, compound 68 stands for (1R,2R,3S)-2-Carbomethoxy-3-(4-t-butyl-phenyl)-tropane, compound 6 stands for (1R,2R,3S)-2-(4-Fluoro-benzoyl)-3-(4-fluorophenyl)-tropane and so on.

Any of these compounds preferably are of the (1R,2R,3S)-configuration. Any of the compounds include pharmaceutically acceptable addition salts thereof.

Most preferred are the compounds of formulae (IA) and (IB)

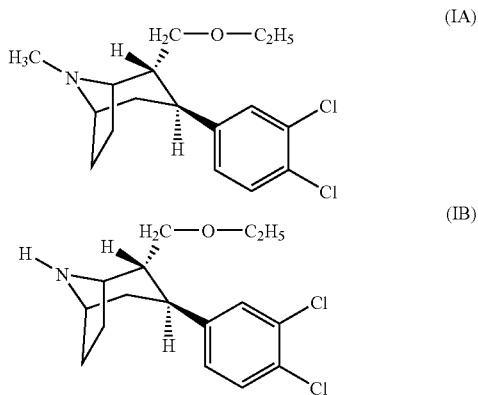

which are coded COMPOUND IA, and COMPOUND IB.

The compounds of the present invention have monoamine neurotransmitter re-uptake inhibitoring effect and comprise a 2,3-disubstituted tropane moiety. They can be used to prepare a pharmaceutical composition for the treatment of diabetes, in particular Type II diabetes. A specific action of the compounds is to lower HbA1c (glycosylated haemoglobin) values, preferably by at least 0.3%, more preferably by at least 0.4% and more preferably by 0.5% within 6 months. The values may be determined either in relation to the starting point or in relation to a placebo group.

Additionally to the effect concerning the lowering of HbA1c, a particular effect of the present invention is that by applying the compound in diabetic patients with overweight, the body weight can be adjusted to normal.

In this context "normal" means that the patients has an average body-mass-index in relation to his age, sex and stage of disease. Accordingly, "overweight" means that the body-mass-index of this person is higher than normal.

Due to this body weight reducing effect in diabetic patients, the compounds also may be used to adjust the body weight of diabetic patients to a level which is regarded as of therapeutic benefit to the patient by the physician.

Preferably the patients are male or female adults of any race.

It is particularly preferred to use the above mentioned monoamine neurotransmitter re-uptake inhibitors comprising a 2,3-disubstituted tropane moiety to prepare a pharmaceutical composition for continuous administration for the treatment or supplemental treatment (co-treatment) of diabetes type II.

The monoamine neurotransmitter re-uptake inhibitors of formulae IA and IB which are preferably used within the scope of the present invention may optionally be used in the form of their pharmacologically acceptable acid addition salts, and optionally in the form of the hydrates and solvates.

By "pharmaceutically acceptable acid addition salts" with respect to the monoamine neurotransmitter re-uptake inhibitors of formula I are meant, according to the invention, those salts which are selected from among the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid, the salts of hydrochloric acid, hydrobromic acid, sulphuric acid, phosphoric acid and acetic acid being particularly preferred. The salts of citric acid are of particular significance, for example in respect to the compounds according to formulae IA and IB. For transdermal administration it is preferable to use the base of formula I.

The monoamine neurotransmitter re-uptake inhibitor comprising a 2,3-disubstituted tropane moiety, preferably the compounds of formula I, most preferably of formula IA and IB, which may be used according to the invention may optionally be used in conjunction with other active substances, in particular antidiabetics drugs. Among such active ingredients are:

Insulin mimetics, meaning compounds expressing the hypoglycemic action through the physiological insulin action, namely the action promoting glucose uptake into cells, in a manner more or less independent to insulin, except for insulin derivatives, and include for example insulin receptor-activating agents (for example, CLX-0901 and L-783281) and vanadium.

Alpha-Glucosidase inhibitors meaning compounds expressing the hypoglycemic action through the suppression of glucose absorption into bodies, mainly via the inhibition of alpha-glucosidase in intestinal tube, and include for example acarbose, voglibose and miglitol.

Glucogenesis inhibitors meaning compounds expressing the hypoglycemic action mainly through the inhibition of glucogenesis, and include for example glucagon secretion suppressors (for example, M&B-39890A and octreotide), fatty acid decomposition inhibitors (for example, nicotinic acid derivatives and carnitine palmitoyltransferase-1 inhibitor) and glucose-6-phosphatase inhibitors.

Other combination partners are inhibitors of renal glucose reabsorption, anti-hyperlipemia agents (for example, HMG-CoA reductase inhibitors and LDL receptor inducers), hypotensive agents (for example, angiotensin converting enzyme inhibitors, angiotensin II receptor antagonists, beta receptor antagonists, alpha 1 or 2 antagonists and calcium antagonists) and the like are also encompassed within the scope of the invention, as long as they can be used in combination with inhibitors of renal glucose reabsorption as a prophylactic and therapeutic agent of diabetes mellitus for the purpose of lowering blood glucose level.

Again, other combination partners are thiazolidinediones (e.g. rosiglitazone, pioglitazone), PPAR-gamma-agonists (e.g. GI 262570), DPPIV inhibitors (e.g. LAF237, MK-431), antagonists, PPAR-gamma/alpha modulators (e.g. KRP 297), protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as to sibutramine or tetrahydrolipostatin, dexfenfluramine, axokine, antagonists of the cannabinoid) receptor, MCH-1 receptor antagonists, MC4 receptor agonists, NPY5 or NPY2 antagonists or β3-agonists such as SB-418790 or AD-9677 and agonists of the 5HT2c receptor, GLP-1 and GLP-1 analogues (e.g. exendin-4) or amylin.

A combination with GABA-receptor antagonists, Na-channel blockers, topiramat, protein-kinase C inhibitors, advanced glycation end product inhibitors or aldose reductase inhibitors may also be used for the treatment or prevention of complications of diabetes.

In accordance with the invention, preferably, the hypoglycemic agent is at least one selected from sulfonylureas (e.g. glibenclamide, tolbutamide, glimepiride, chlorpropamide, glipizide, gliclazide), meglitinide analogues and biguanides (e.g. metformin, phenformin and buformin). In an embodiment of the invention, additionally, the hypoglycemic agent is preferably at least one selected from sulfonylureas and biguanides.

In another embodiment of the invention in view of combinations the antidiabetic agent is preferably a meglitinide analogue.

In another embodiment of a combination according to the invention the antidiabetic agent is preferably a glinide such as nateglinide, repaglinide.

Beside such antidiabetic ingredients other combination partners may be $D_1$-, $D_2$-, $D_3$- or $D_4$-agonists and/or anorectics and/or lipase inhibitors and/or sympathomimetics. Among the preferred combination partner are: Rimonabant, adrogolide, A-86929, rotigotine, NeurVex, nolomirole, pramipexole, talipexol, CHF 1512, (–)-stepholidine, DAR-201, diacrin/Genzyme, bromocriptine, bupropion, LEK-8829, BAM-1110, AIT-203, terguride, aripiprazole, OPC-4392, GMC-1111, PD-148903, apomorphine HCl, PD-89211, PD-158771, cabergoline, sumanirole, PNU-14277E, POL-255, dihydrexidine, GBR-12783, quinagolide HCl, (R)-bupropion, S-32504, S-33592, SKF-80723, SKF-83959, fenoldopam, ropinirole, SKF-82958, SKF-77434, DU 127090, SLV-308, SLV 318, NeuroCRIB, SP-1037C, spheramine, gallotrank, preclamol, DAB-452, YM-435, BP-897, ProSavin, etilevodopa, P63, A 68930, A 77636, alaptide, alentemol, CI 1007; PD 143188, BLSI, JA 116a; JA 116, melevodopa; levodopa methyl; CHF 1301; NSC 295453; levomet, MR 708, PD 128483, RD 211, SKF 38393, SKF 81297, U 86170F, U 91356A, WAY 124486, Z 15040, sibutramine, orlistat, amfepramon-HCl and ephedrine.

From the aforementioned combinations a combination of a compound according to the present invention with rimonabant is preferred in particular with regard to the treatment of persons with overweight, in particular persons suffering from diabetes.

The compound according to the invention, or a physiologically acceptable salt thereof, and the additional active substance to be combined therewith may both be present together in one formulation (fixed combination), for example a tablet or capsule, or separately in two identical or different formulations (free combination), for example as a so-called kit-of-parts.

The dosage of the monoamine neurotransmitter re-uptake inhibitor comprising a 2,3-disubstituted tropane moiety according to the invention is naturally highly dependent on the severity of the symptoms to be treated on the one hand and the choice of active substance on the other hand. For example, without restricting the subject matter of the present invention thereto, some possible dosages especially for the compounds of formula IA and IB which are particularly preferred according to the invention will now be given. This may be used in dosages of about 0.05 to 10 mg, preferably about 0.1 to 2.0 mg, in particular about 0.25 to 2.0 mg daily. These dosages are based on the compound of formula IA in the form of its free base. Based on the salt form which is preferably used, namely the citrate, the above mentioned dosages correspond to about 0.08 to 16 mg, preferably 0.16 to 3.2 mg, in particular about 0.4 to 3.2 of the compound of formula IA citrate per day.

The monoamine neurotransmitter re-uptake inhibitors comprising a 2,3-disubstituted tropane moiety may be administered for the purposes according to the invention by oral, rectal, transdermal, intrathecal, inhalative, nasal or parenteral route, preferably by oral or transdermal, most preferably by oral route. Suitable preparations include, for example, tablets, capsules, suppositories, solutions, syrups, emulsions, dispersible powders, implants or plasters, most preferably tablets. Tablets may be obtained, for example, by mixing the active substance or substances with known excipients, e.g. inert diluents such as calcium carbonate, calcium phosphate or lactose, disintegrants such as maize starch or alginic acid, binders such as starch or gelatine, lubricants such as magnesium stearate or talc, and/or agents for obtaining delayed release such as carboxymethylcellulose, cellulose acetate phthalate, or polyvinylacetate. The tablets may also consist of several layers.

Due to the therapeutically positive effects of the compound in diabetic patients, the compound also may be used in diseases which develop as a consequence of diabetes like retinopathy, nephropathy or neuropathies, diabetic pain, in particular diabetic neuropathic pain, in particular peripheral diabetic neuropathic pain, diabetic foot, ulcers, macroangiopathies. Among such concomitant diseases the treatment of peripheral diabetic neuropathic pain, retinopathy and/or nephropathy are preferred. Most preferred are retinopathy and/or nephropathy.

The invention claimed is:

1. A method for the treatment of Type 2 diabetes, which method comprises administration to a patient in need thereof effective amounts of the compound of formula (IA):

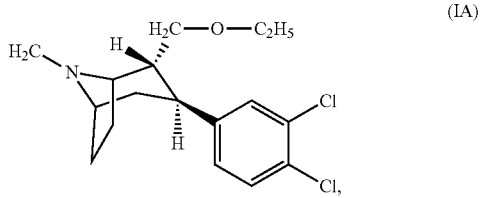

(IA)

a pharmaceutically acceptable salt, solvate, or physiologically functional derivative thereof.

2. The method according to claim 1, wherein the dosage amount of said compound of formula (IA) is administered from 0.05 to 10 mg daily.

3. The method according to claim 1, wherein said compound of formula (IA) is administered by an oral, injectable, transdermal or rectal route.

4. The method according to claim 1, wherein said compound of formula (IA) lowers the HbA1c value in a diabetic patient.

5. The method according to claim 1, wherein said compound of formula (IA) is administered in fixed or free combination with at least one antidiabetic agent that treats Type 2 diabetes.

6. The method according to claim 1, wherein said compound of formula (IA) is administered in combination with Rimonabant.

7. A method for lowering HbA1c values in a diabetic patient, which method comprises administration to a patient in need thereof effective amounts of the compound of formula (IA):

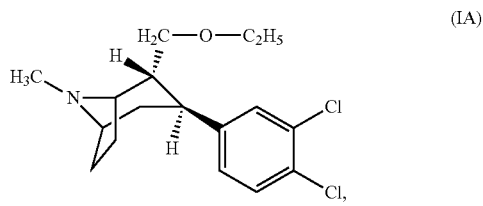

(IA)

a pharmaceutically acceptable salt, solvate, or physiologically functional derivative thereof.

8. The method according to claim 7, wherein the administration is an oral, injectable, transdermal or rectal route, the dosage amount of said compound of formula (IA) is from 0.05 to 10 mg daily, and the compound of formula (IA) is administered in fixed or free combination with at least one antidiabetic agent that treats Type 2 diabetes.

9. The method according to claim 7, wherein HbA1c is lowered in said patient by at least 0.5% within 6 months of administration.

10. A method for the treatment of Type 2 diabetes, which method comprises administration to a patient in need thereof effective amounts of the compound of formula (IA)

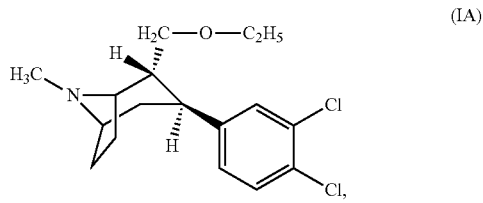

(IA)

a pharmaceutically acceptable salt, solvate, or physiologically functional derivative thereof;
wherein said compound of formula (IA) is administered in combination with Rimonabant.

11. The method according to claim 10, wherein the dosage amount of said compound of formula (IA) is administered from 0.05 to 10 mg daily.

12. The method according to claim 10, wherein said compound of formula (IA) is administered by an oral, injectable, transdermal or rectal route.

13. The method according to claim 10, wherein said compound of formula (IA) lowers the HbA1c value in a diabetic patient.

* * * * *